(12) United States Patent
Barker et al.

(10) Patent No.: US 9,762,039 B2
(45) Date of Patent: Sep. 12, 2017

(54) CABLE INSTALLATION DETECTION

(75) Inventors: Philip A. Barker, Ipswich (GB);
Graham A Laidler, Ipswich (GB)

(73) Assignee: BRITISH TELECOMMUNICATIONS PUBLIC LIMITED COMPANY, London (GB)

( * ) Notice: Subject to any disclaimer, the term of this patent is extended or adjusted under 35 U.S.C. 154(b) by 2129 days.

(21) Appl. No.: 12/295,750

(22) PCT Filed: Apr. 2, 2007

(86) PCT No.: PCT/GB2007/001216
§ 371 (c)(1),
(2), (4) Date: Oct. 2, 2008

(87) PCT Pub. No.: WO2007/113544
PCT Pub. Date: Oct. 11, 2007

(65) Prior Publication Data
US 2010/0148138 A1    Jun. 17, 2010

(30) Foreign Application Priority Data

Apr. 3, 2006   (EP) ..................... 06251871

(51) Int. Cl.
*H02G 1/08*   (2006.01)
*G01R 27/28*   (2006.01)
(Continued)

(52) U.S. Cl.
CPC .................. *H02G 1/08* (2013.01); *F16L 7/00* (2013.01); *F16L 55/48* (2013.01); *G01N 29/024* (2013.01);
(Continued)

(58) Field of Classification Search
CPC .......... H02G 1/08; H02G 1/081; H02G 1/086; F16L 7/00; F16L 55/48; F16L 2101/50;
(Continued)

(56) References Cited

U.S. PATENT DOCUMENTS

| 4,471,651 A | 9/1984 | Dimeff et al. |
| 4,880,484 A | 11/1989 | Obermeier et al. |

(Continued)

FOREIGN PATENT DOCUMENTS

| DE | 42 02 147 | 7/1993 |
| DE | 103 38 950 | 6/2005 |

(Continued)

OTHER PUBLICATIONS

International Search Report for PCT/GB2007/001216, mailed Jul. 19, 2007.

*Primary Examiner* — Hadi Shakeri
(74) *Attorney, Agent, or Firm* — Nixon & Vanderhye PC (57) ABSTRACT

A method for use in connection with installing a cable into a conduit having a first conduit end and a second conduit end, comprising the steps of —providing the cable with a metallic attribute, —providing within or proximate to the conduit, sensing means for sensing the metallic attribute, —introducing the cable into the first conduit end and driving it towards the second conduit end and —detecting that the sensing means has sensed the metallic attribute by sensing a change in inductance levels of the sensing means.

11 Claims, 6 Drawing Sheets

(51) Int. Cl.
  *F16L 7/00* (2006.01)
  *F16L 55/48* (2006.01)
  *G01N 29/024* (2006.01)
  *G01N 29/22* (2006.01)
  *G02B 6/44* (2006.01)
  *F16L 101/50* (2006.01)

(52) U.S. Cl.
  CPC ............ *G01N 29/222* (2013.01); *G02B 6/447* (2013.01); *G02B 6/4464* (2013.01); *H02G 1/081* (2013.01); *H02G 1/086* (2013.01); *F16L 2101/50* (2013.01); *G01N 2291/012* (2013.01); *G01N 2291/02836* (2013.01); *G01N 2291/044* (2013.01); *G01N 2291/056* (2013.01)

(58) Field of Classification Search
  CPC ............... G01N 29/024; G01N 29/222; G01N 2291/012; G01N 2291/02836; G01N 2291/056; G01N 2291/044; G02B 6/4464; G02B 6/447
  USPC ...... 254/134.3 R, 134.4, 134.3 FT, 134.4 FT
  See application file for complete search history.

(56) References Cited

U.S. PATENT DOCUMENTS

| | | | | |
|---|---|---|---|---|
| 5,248,128 | A * | 9/1993 | Warren et al. | ............. 254/134.4 |
| 5,467,968 | A * | 11/1995 | Proud et al. | ............... 254/134.4 |
| 6,364,290 | B1 * | 4/2002 | Barker | ....................... 254/134.4 |
| 6,480,635 | B1 | 11/2002 | Russell et al. | |
| 7,225,533 | B2 * | 6/2007 | Sylvia et al. | .............. 254/134.4 |
| 7,562,861 | B2 * | 7/2009 | Fee et al. | ................... 254/134.4 |
| 2002/0034365 | A1 | 3/2002 | Vogelsang | |

FOREIGN PATENT DOCUMENTS

| | | |
|---|---|---|
| EP | 0 294 243 | 12/1988 |
| FR | 2 737 053 | 1/1997 |
| GB | 2 073 440 | 10/1981 |
| JP | 04-240806 | 8/1992 |
| JP | 08-163737 | 6/1996 |

* cited by examiner

CABLE INSTALLATION DETECTION

This application is the U.S. national phase of International Application No. PCT/GB2007/001216 filed 2 Apr. 2007 which designated the U.S. and claims priority to EP 06251871.7 filed 3 Apr. 2006, the entire contents of each of which are hereby incorporated by reference.

BACKGROUND AND SUMMARY

The present invention relates to the installation of cables, such as optical fibre units, wires, electrical cables or the like. More specifically, but not exclusively, the present invention relates to the blowing of fibre unit cables through pre-laid conduits.

Optical fibres are widely used within telecommunication systems for high-speed information transfer. A fibre unit, which could comprise a single optical fibre, or a bundle of optical fibres, is commonly installed into a protective optical conduit comprising optical fibre tubes, which have already been laid along the desired route, usually as a continuous span between convenient access points such as surface boxes or inspection chambers.

In this description, references to "cables" shall include where the context permits, individual optical fibres and fibre units as well as cables comprising such fibres and fibre units. "Conduits" shall include tubes and tube bores, but in the main refers to the route or path populated or to be populated by a fibre cable, and where the route comprises a number of tubes, the entire length of the route.

The conduits typically are made of plastic, each with a typical inner diameter of 3 to 6 mm or more, and are usually provided in a bundle comprising up to 24 or more tubes, which are held together within a protective outer sheath. Each fibre conduit tube can receive at least one fibre unit comprising one or more individual optical fibres. Large numbers of conduits—and bundles of conduits—are pre-installed across the access network and the distribution network between the local exchanges and the customer premises in a branching network system. With the advent of fibre to the premises (FTTP), the conduits will further extend to and into commercial and residential premises. Indeed it is a fundamental part of the push to FTTP in e.g. the UK that substantially all the network comprises optical fibre, extending from the core network to as many end customers as possible. To achieve this, optical fibre installation needs to be speedy, cost- and effort-efficient.

In the vast majority of cases, a dedicated path is described between two points with a single length of conduit tube. In an exceptional case, the conduit path may comprise a number of lengths of physically separate conduit tubes which are connecterised together in series with tube connectors. Choosing the correct conduit tube at the installation should in the normal case, result in the fibre unit emerging at the other end.

Problems however may arise which result in the fibre unit not reaching the correct destination. During installation, the operator is usually presented with a large number of conduit tubes, which could result in a mistake in identifying the correct conduit, especially if the operator is working in adverse conditions down a manhole or in poor lighting. This may be so even where conduits are coloured coded which helps to direct the operator to the correct conduit.

There is also the possibility that a conduit route is wrongly mapped in the records used by the operator so that one end of the conduit does not lead to the correct destination. Where the path comprises a number of tube lengths connectorised together in series, yet another problem may lie in broken connections between lengths of conduit tubes within the network, so that the fibre unit may get lost within the system during installation and never emerge at the destination. Yet another issue may be the possibility that the fibre unit, during installation, could be impeded by an imperfect connector or a tight bend or some other source of friction in the conduit, and again never emerge at the destination.

For any of these or other reasons, the fibre unit will emerge in the wrong place, or not at all. Add to that some uncertainty about the exact length of the conduit route down which the fibre unit is being installed, so that the operator cannot even accurately know in a timely manner when something has gone wrong.

One method of installing fibre units into the conduits is by pulling them through the conduits. However, the tension induced can cause damage to the fibre units and impair their operating performance. A known alternative method is the "blown fibre" technique whereby a compressed fluid such as compressed air is used to convey, or "blow", a fibre unit along a conduit from one end.

Currently, installing fibre units using the blown fibre method requires at least two operators: one situated at the head end of the conduit, where during installation air and the fibre unit are installed into the mouth of the conduit, and one at the remote end of the conduit, where air and the fibre unit emerge from the mouth of the conduit. The second remote end operator is required because the remote end is often some distance away—up to a kilometer or more—from the head end. The operator at the head end is therefore unable to know the status of the remote end during an installation without a second operator located there.

The head end operator monitors and operates a fibre installation mechanism—known in the art as a "blowing head"—that feeds the optical fibre into the conduit and controls the supply of compressed air. He starts the process by directing air into the mouth of the head end conduit. If the air is directed into the correct conduit, the remote end operator will sense the arrival of the air with an air flow meter temporarily connected to the end of the conduit, or more simply by feeling the air flow exiting the conduit against his hand if the air flow is sufficiently high. He then communicates this to the head end operator by radio or other means, to confirm to the head end operator that he is applying air to the correct conduit. The head end operator then introduces the fibre unit into the conduit and blows it through to the remote end of the conduit, whereupon the remote end operator advises his colleague on its arrival. The head end operator then turns off the air supply and the blowing head, and the process is complete.

This process is labour-intensive as a minimum of two operators must work on a single installation. The head end operator needs to be skilled in the operation of the blowing head, while the remote end operator is required to alert his colleague to the status of the installation at the remote end.

Methods whereby a single operator at the head end of a conduit can detect the arrival of an optical fibre at the remote end of the conduit are known.

In the simplest method, the length of the conduit route is known, allowing the operator to know that the fibre has (probably) arrived at the remote end when the required length of fibre unit has been played out. This relies on the map record of conduit route being up to date and accurate, and presumes a completely smooth and obstruction-free conduit route. Neither of these can be guaranteed in practice.

Another known practice is to install at the remote end of the conduit a barrier of porous material such as an "airstone"

which is placed at the remote end of the conduit, which will allow air through but which will stop further progress of the fibre unit. This cease in progress is detected by the blowing head which then stops further ingress. However even when the progress of the fibre has ceased, the operator at the head end cannot be certain that the fibre unit has reached the porous barrier at the end of the conduit, or if instead the fibre unit is caught on an obstruction at some point along the length of the conduit.

As described in WO9103756, a solution is to position a light source at the remote end of the conduit and a light detector is positioned at the head end. The arrival of the optical fibre at the remote end is indicated by the detection of light by the detector at the head end. One problem with this method is that an early, or "false", indication of the arrival of the optical fibre may occur if stray light is inadvertently introduced into the conduit at a location between the head end and remote end, e.g. at an open inspection chamber. This method also relies on adequate light being coupled into the advancing end of the optical fibre to be detected by the detector, however the coupling process is inefficient and is further degraded in proportion to the length of the optical fibre due to normal attenuation properties, so this method may not be practicable on long lengths of optical fibre. A second method described in this document uses a previously installed optical fibre to create part of a light "circuit" with the blown optical fibre. This method is not as suitable for installing the first optical fibre in a conduit. Furthermore, any previously installed fibre units may be carrying live traffic and so would not be available to use for the installation of additional fibres.

Another known method is to use a blowing head such as that described in WO/9812588, which is configured to stop driving the fibre unit when it senses that fibre movement within the conduit is slowing down or stopping owing to an obstruction. When used in conjunction with a porous airstone at the remote end, the fibre unit would stop moving when it reaches the destination end. However, as the sealed-off end is just one type of obstruction the fibre unit may encounter on the conduit route, this method fails to positively identify when the fibre unit has reached and emerged from the conduit at the remote end without travelling to the remote end for a visual inspection.

Accordingly, in a general aspect, the present invention provides methods and devices for aspects relating to the installation of cables such as fibre units into conduit tubes, in particular, allowing a single operator to operate substantially on his own to determine if air fed into a conduit is reaching its intended destination, and/or if and when the fibre unit fed into the conduit has reached its destination. The invention can be used where the operator has to choose one of a number of conduits, or where there is a single conduit but where it is desirable to unambiguously confirm that the air and fibre unit reaches the intended destination.

A first aspect of the invention provides a method for use in connection with installing a cable into a conduit having a first conduit end and a second conduit end, comprising the steps of
 providing the cable with a metallic attribute,
 providing within or proximate to the conduit, sensing means for sensing the metallic attribute,
 introducing the cable into the first conduit end and driving it towards the second conduit end, and
 detecting that the sensing means has sensed the metallic attribute by sensing a change in inductance levels of the sensing means.

By using this method, a fibre bead detection system can be set up to send a signal to an operator situated at the head end of the cable tube installation to indicate or confirm if and when the fibre unit fed into the conduit at the head end has arrived at the remote end. The metallic attribute can be an inherent part or property of the cable, although conveniently it is provided in the invention in the form of a metal sleeve or a bead capable of actuating the sensor, which can be placed at any point along the length of the cable. If the method is to serve to signal arrival of the fibre at the remote end, the actuator can be positioned at the advancing end or tip of the cable.

A variety of metals can be sensed or detected by changes in inductance levels of a sensor such as an induction coil. In a preferred version of the invention, a change in the frequency oscillation of an LC oscillator is sensed.

The skilled person would also appreciate that the method can be used to detect the electromagnetic actuator itself, or any object or article to which the actuator is attached.

A second aspect of the invention provides a device for use in connection with installing a cable provided with a metallic attribute, into a conduit having a first conduit end and a second conduit end, comprising
 sensing means for sensing the metallic attribute, and
 detecting means to detect that the sensing means has sensed the metallic attribute by sensing a change in inductance levels of the sensing means.

The device is preferably adapted to be used with a metallic actuator. If it is used to detect fibre unit arrival, it should preferably be coupled to the conduit at its remote end. In such a case, one embodiment of the invention is a device with a bore communicating with the conduit so that the fibre can enter the bore to allow for its presence to be sensed by the detecting means.

Alternatively, the device can be fitted anywhere else along the conduit, to detect the fibre coupled to the actuator, or else to track the movement or location of the fibre in a network of conduits. Thus, the device of the invention can be used for tracking or detection in other applications or contexts where an item with a metallic property or attribute is moving within a conduit or container or even outside containment means. The device can also be configured for the detection of speed of movement of the metallic actuator.

Preferably, the device includes means to contain the actuator in such a way that the detecting means is as close as possible for greater sensitivity. The sensing means can comprise any means sensitive to a metallic attribute, but in the embodiment it can comprise an LC oscillator including an inductive loop.

A third aspect of the invention provides a device for use in connection with installing a cable into a conduit having a first conduit end and a second conduit end, the cable including sensing means for sensing a metallic attribute, comprising
 a metallic actuator, and
 detecting means to detect that the metallic actuator has been sensed by the sensing means by sensing a change in inductance levels of the sensing means.

It is within the scope of the invention for the sensing means and the actuator to be located in the other's place i.e. the sensing means can be associated with the fibre unit cable, and the actuator positioned where it is desired to sense the presence of the fibre unit or other object to which the actuator is coupled.

A fourth aspect of the invention provides a metallic actuator for use in connection with installing a cable into a conduit having a first conduit end and a second conduit end, the actuator comprising a body for securing to the cable, and suitable for use with a device comprising sensing means for sensing the metallic attribute, and detecting means to detect that the sensing means has sensed the metallic attribute by sensing a change in inductance levels of the sensing means.

As noted above, this can be any device having the necessary metallic attribute to allow it to be sensed by the sensing device, and which can be coupled to the fibre unit or other object. Thus, although it is described below as a bead connected to the advancing tip of the fibre, it could for example, take the form of a sleeve, or an adhesive strip or sheet, or some kind of substance which can be painted on the object to be sensed. The skilled person would understand that the invention includes the sensing of the actuator itself moving though the medium (which in a blown fibre installation comprises air), so the actuator could be used to sense the presence, movement and speed of the medium at a particular section within the conduit, or conduit network, as the case may be.

A fifth aspect of the invention provides a metal sensor for use in connection with installing a cable into a conduit having a first conduit end and a second conduit end, the sensor comprising a body for securing to the cable, and being suitable for use with a device comprising a metallic actuator, and detecting means to detect that the metallic actuator has been sensed by sensing a change in inductance levels of the sensor.

This aspect of the invention is a sensor which can be coupled to the fibre unit or other object, which can be used with the device of the third aspect of the invention as described above. Used together, the sensor and the actuator provide the necessary change in the sensor and/or actuator to allow an operator to detect the presence of the actuator and thus the fibre unit or other object to which the sensor is connected to.

A sixth aspect of the invention provides an installation for installing a cable using an air flow into a conduit having a first conduit end and a second conduit end, comprising an air source to introduce air into the conduit at the first conduit end, driving means to mechanically drive the cable through the conduit, and cable presence detection means comprising a device including sensing means for sensing a metallic attribute of the cable, and detecting means to detect that the sensing means has sensed the metallic attribute by detection of a change in the inductance levels of the sensing means, and a metallic actuator comprising a body for securing to the cable.

A blown fibre installation includes other apparatus: an air compressor to supply pressurised air into the conduit, and a blowing head including drive wheels to mechanically drive the fibre unit into the conduit. The devices of the invention can be advantageously used in such an installation to provide an operator with information about the location of the fibre unit or the actuator.

A seventh aspect of the invention provides a method for use in connection with installing a cable using an air flow into a conduit having a first conduit end and a second conduit end, comprising (i) a method to detect the air flow at the second conduit end, comprising the steps of introducing the air flow into the conduit, introducing a signal into the conduit, or into a bore communicating with the conduit, and detecting a change in a property of the signal caused by movement of the air flow, and (ii) a method comprising the steps of providing the cable with a metallic attribute, providing within or proximate to the conduit, sensing means for sensing the metallic attribute, introducing the cable into the first conduit end and driving it towards the second conduit end, and detecting that the sensing means has sensed the metallic attribute by detection of a change in the inductance levels of the sensing means.

By using this method, an operator can first obtain a positive indication that air is flowing to and from the correct remote end of the conduit by using a phase shift' detection method, then immediately follow up with feeding the fibre unit into the identified conduit at the head end, and upon learning that the fibre unit fitted with the actuator has reached the far end, the installation session can be terminated. The method can also be used to track air or fibre location within the conduit or network of conduits, as well as to sense speeds of movement of the air and/or fibre unit.

An eighth aspect of the invention provides a device for use in connection with installing a cable using an air flow into a conduit having a first conduit end and a second conduit end, comprising (i) a device to detect of the air flow at the second conduit end, comprising a transmitter for transmitting a signal into the conduit, and a detector to detect a change in a property of the signal caused by movement of one or both of the air flow and the cable, and (ii) a device comprising sensing means for sensing the metallic attribute, and detecting means to detect that the sensing means has sensed the metallic attribute by detection of a change in the inductance levels of the sensing means.

The device in his aspect incorporates the means to sense and detect a phase shift created by movement of air or of the fibre unit within the conduit, as well as an electromagnetic change brought about by the proximity of the electromagnetic sensor and electromagnetic actuator.

A further aspect of the invention provides an installation for installing a cable into a conduit having a first conduit end and a second conduit end, comprising (i) an installation comprising an air source to introduce air into the conduit at the first conduit end, driving means to mechanically drive a cable through the conduit, a transmitter for transmitting a signal into the conduit, and a detector to detect a change in a property of the signal caused by movement of one or both of the air flow and the cable, and (ii) an installation comprising an air source to introduce air into the conduit at the first conduit end, driving means to mechanically drive the cable through the conduit, and cable presence detection means comprising either a device including sensing means for sensing the metallic attribute, and detecting means to detect that the sensing means has sensed the metallic attribute by detection of a change in the inductance levels of the sensing means, used in conjunction with a metallic actuator comprising detecting means to detect that the sensing means has sensed the metallic attribute by detection of a change in the inductance levels of the sensing means.

The installation for a blown fibre installation advantageously includes the devices and means for air and the fibre unit to be fed into the conduit at the head end, and for such air and fibre unit to be detected at the remote end.

BRIEF DESCRIPTION OF THE DRAWINGS

Preferred embodiments of the invention will now be described, by way of example only, with reference to the accompanying drawings, in which.

DETAILED DESCRIPTION OF PRESENT EXAMPLE EMBODIMENTS

Figure 1:
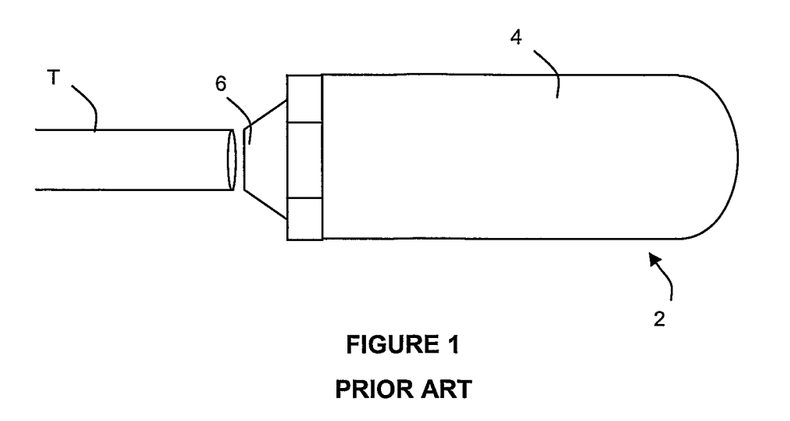
FIG 1 depicts an airstone of the prior art.

FIG 1 shows a prior art "airstone" (2), which is used in current blown fibre installations. As noted above, the airstone is connected to the remote end of the conduit. It comprises a housing (4) which is substantially cylindrical and which is rounded at one end. At the other end is a collar (6) which permits the airstone to be connected to an optical fibre tube (T) by friction fit. The housing comprises a compressed granular body which allows air to flow from the fibre tube (T) into, and then out of the airstone, via the housing.

Figure 2:
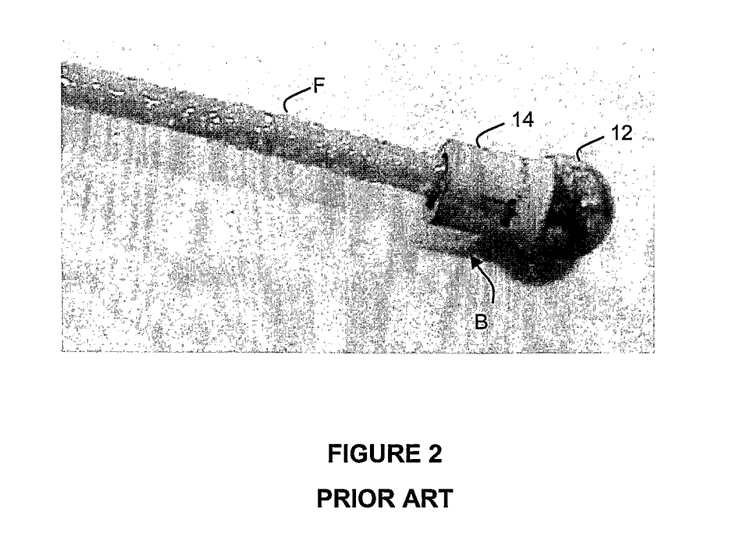
FIG 2 depicts a fibre bead of the prior art.

FIG 2 depicts a prior art fibre "bead" (10). It comprises a head portion (12), a neck (14), and includes a slot within it to accommodate the tip or leading end of the fibre unit (F). It is typically made of a metal such as brass or aluminium, which is corrosion-resistant and sufficiently malleable to be crimped at the neck (14) onto the end of the fibre unit (1) by an operator using pliers. Where rusting is not an issue, ferrous materials such as steel can also be used. After use when the fibre has reached the remote end of the installation, the bead is cut off and discarded. Its main function is to protect the leading end of the fibre during installation, from bumping into the sides of the tube, and from damage when the leading end reaches the airstone (2), and to ensure a smooth path through fibre tube connectors.

Figure 3A:
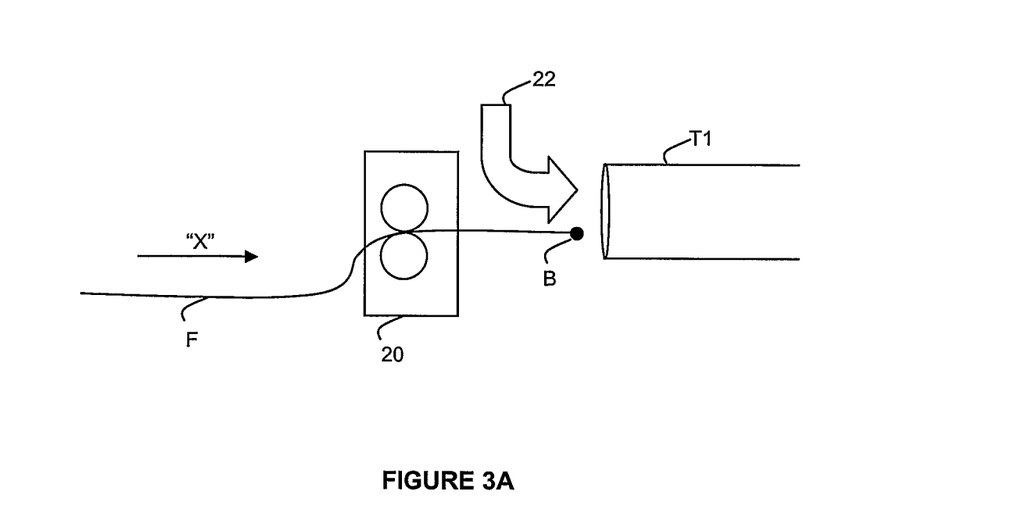
FIGS. 3A and 3B are respectively views of the head and remote ends of a blown fibre installation according to the invention.
Figure 3B:
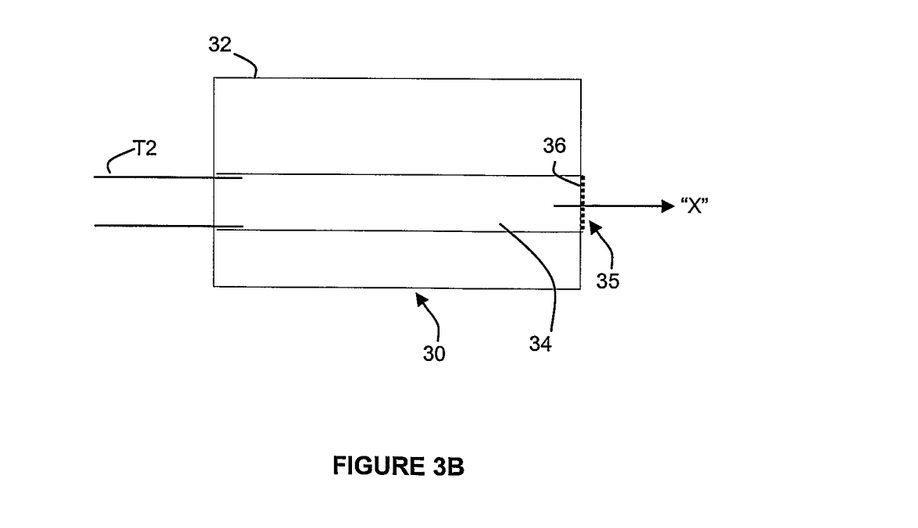

The apparatus and set up for a typical blown fibre installation is shown in FIGS. 3A and 3B. The head end of the installation is depicted in FIG 3A, where the head end tube (T1) is fed with an air supply (22) and the fibre unit (F) in the direction of arrow "X". A blowing head (20) is attached to the tube, which provides a mechanical pushing force via drive wheels, to drive the fibre unit (F) through the tube (T1). The air compressor supplying the air (22) is connected to the blowing head so that the air is channelled into the tube via the blowing head. The fibre unit is driven along the conduit by a combination of the viscous drag generated by the air flowing along the conduit, and the drive wheels of the blowing head.

In FIG 3B, the remote end of the conduit (T2) can be the other end of the same tube (T1) or a physically separate tube connectorised at an immediate point. In an embodiment of the invention, a sensing device (30) is connected to the remote end tube (T2). This comprises a housing (32) and includes a bore (34) to which the outlet end of tube (T2) can be fitted, the bore terminating in a bore end (35). Air and fibre fed into the conduit from the head end can enter the bore in the direction of arrow "X". The sensing device includes means for the air to escape from the device in the form of a disc of porous material (36) located at the bore end (35). The disc (36) can be made from the same ° material as that for a conventional airstone (2) or other suitable materials, so that the fibre end retained within the device while the air may flow freely out of the bore. The means for air escape could also be located elsewhere within the device, and the means could alternatively comprise vents. Another alternative, but less preferred way, would be to connect a conventional airstone (2) to the bore end (35) so that it projects from the device (30).

In a typical blown fibre installation according to the invention, the operator connects a sensing device (30) to the remote end of the conduit tube through which the fibre unit is to emerge. He then returns to the head end to start the blown fibre installation process. The operator first determines that air introduced into the head end of the conduit does flow to the desired remote end, before introducing the optical fibre into the conduit (T1). He turns on the compressor located at the head end to generate the air flow (22 in FIG 3A) into the conduit, and if all is well (i.e. the operator has chosen the correct conduit, the conduit route is correctly mapped, etc.), the air flows in the direction of arrow "X" through the conduit to the remote end of the conduit as shown in FIG 3B.

The air flows to and out of the mouth of the conduit (T2) and into the sensing device (30) connected to the conduit. At this stage, the fact of air arrival could be alerted to the operator at the head end by e.g. a radio signal sent from the remote end.

After the operator has determined that air is indeed flowing to the correct remote end, the optical fibre unit (F) is fitted with a fibre bead (B in FIG 2) and then introduced into the head end of the conduit. The fibre unit is driven along the conduit by a combination of the viscous drag generated by the air flowing along the conduit, and the drive wheels of the blowing head (20).

In FIG 3B, the device 30 is shown as being positioned at the mouth of the remote end of the conduit, in place of the conventional airstone (2 in FIG 1). Although this is a preferred position, the device can be positioned in other places to realise the advantages of the invention, as will be described below.

Two problems in particular are addressed by the device according to the invention: first, the determination that air fed into the head end of the conduit using the compressor has arrived at the remote end, and second, that the fibre unit fed into the head end has arrived at the remote end. By using the device and methods described herein, a single operator located at the head end of the conduit may positively know whether air has been fed into the correct tube, and when the fibre unit has reached the remote end.

Figure 4:
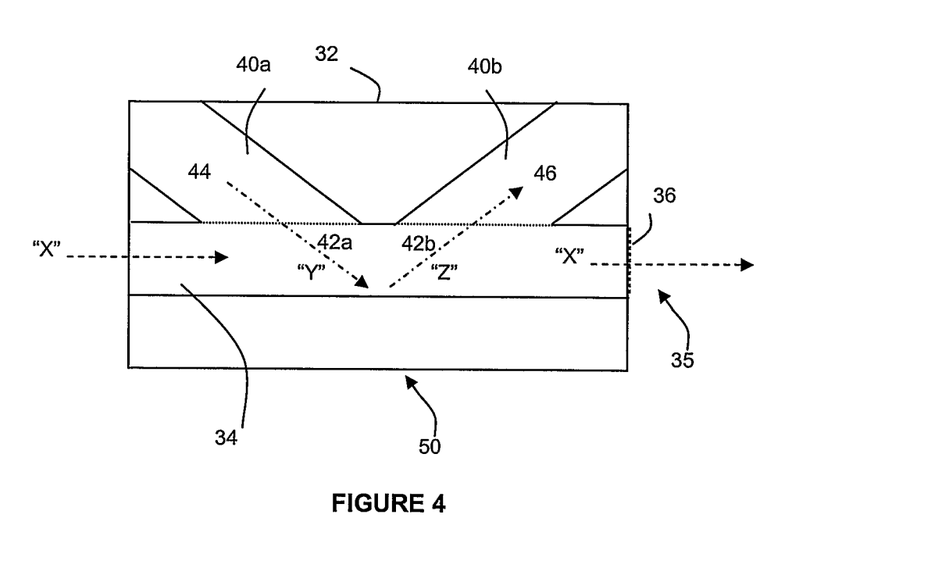
FIG 4 is a cross section view of an embodiment of a device for sensing air arrival.

FIG 4 is a cross sectional view of one embodiment of a sensing device (50) according to the invention. This device can take the size and proportions of a matchbox, and be made of a cost-efficient material such as a plastic. It will be installed on the remote end of the conduit on tube (T2 in FIG 3B) prior the start of the blown fibre installation session, by a simple push-fit or the like.

As described earlier against FIG 3A, the housing (32) includes a bore (34) though which air and the fibre can enter. The device further includes acoustic channel entrance and exit sections (40a, 40b). The acoustic entrance and exit channels are in this embodiment set at about 30 degrees to the longitudinal axis of the device bore (34), and intersect and interface with the device bore as shown to form an acoustic channel comprising an entrance, bore and exit section; the total physical length of the acoustic channel is approximately 250 mm.

During use of the sensing device, a mechanical wave signal such as an acoustic or sound signal (42) is transmitted as a transmitted signal (42a) along the first, transmission acoustic channel (40a) in the direction of arrow "Y". The transmitted signal (42a) is reflected at the floor of the device bore (34) and transmitted at an angle of about 30 degrees along the second, reception acoustic channel (40b) in the direction of arrow "Z" as a reflected received signal (42b).

The acoustic signal (42) is generated using a suitable signal generator and transmitted with a miniature loudspeaker—these functions can be performed with a single device (44). The received signal (42b) is received within the reception channel (40b) by a receiver (46)—this could be a miniature microphone. The transducers (the acoustic signal generator/transmitter and receiver) are small units which can be located within the acoustic channels so that the entrances to the channels are sealed off from the bore as shown. The signals are measured and compared by e.g. a processor. In the present embodiment, the processor drives the transmitter with a square wave at 40 kHz and detects the received signal, after amplification, as another square wave of differing phase; the actual phase shift is determined by measuring the time between the leading edge of each driving pulse and the next occurring leading edge of the received amplified signal.

As the signals within the acoustic channels comprise sound waves travelling through air, disturbance of the air medium through which the sound waves are travelling will cause a phase shift. Where the air flow is travelling in the direction of arrow "X", the sound path is reduced, and the phase angle of the acoustic wave shifted. The phase angle reduces approximately proportionally with the speed of the air flow.

In an example where the acoustic path length of the acoustic signal is about 25 cm from transmitter (44) to receiver (46), and where the portion of the acoustic path within the bore (34) is about 10 cm, it will take about 0.00075 seconds for a 40 kHz wave travelling at a rate of about 330 m/s, to travel from the transmitter to the receiver though unmoving air within the bore. When air arrives at and starts flowing through the bore, the transmitted signal (42a) is carried by the air moving within the bore. The frequency of the received signal (42b) detected by the receiver is the same, but is shifted in time.

Figure 5:
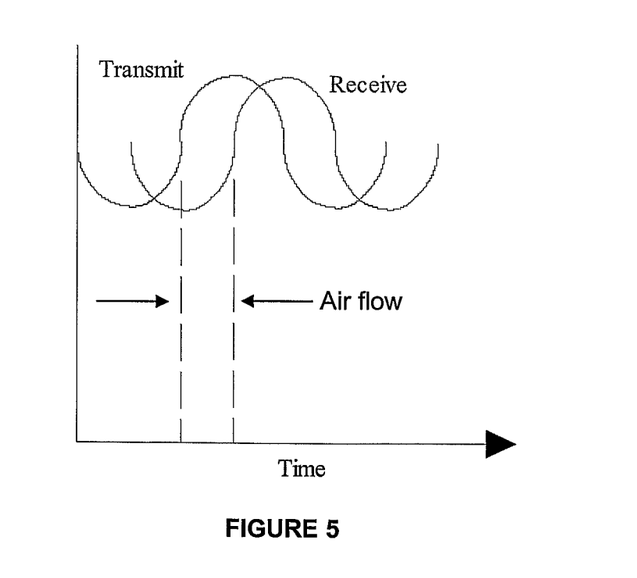
FIG 5 is a graph illustrating how air flow arrival and speed is detected.

FIG 5 is a graph illustrating the shift in phase caused by the movement of the air medium when the acoustic signal is travelling through the bore. Thus detection of a phase shift is an indication that air is flowing within the device bore. By measuring the phase shift or angle change, it is further possible to measure the speed at which the air is travelling within the bore.

This embodiment of the device of FIG 4 is designed so that the maximum expected change in phase shift (i.e. between the phase shift when air is stationary within the acoustic channel and when air is flowing at its maximum expected speed in the forward direction—i.e. towards the receiver) is definitely less than one wavelength (otherwise there could be two different possible air speeds corresponding to the same phase shift) and preferably less than half of a wavelength (so that "negative" air speeds—i.e. where the air is travelling in the direction from the receiver to the transmitter). In the present embodiment the maximum expected air speed is about 10 m/s (an expected maximum throughput of air is 20 liters per minute for an 8 mm internal diameter conduit, which corresponds to about a speed of 7 m/s). In the present embodiment a sonar signal of frequency 40 kHz is used which gives rise to a wavelength of approximately (330 m/s)/(40 kHz) (λ=v/f)≈8.25 mm and thus a half wavelength of about 4 mm. The acoustic path length, $I_a$, within the bore is given approximately by:

$$I_a = I_b \cdot v_s / (v_s + v_m)$$

where $I_b$ is the physical length of the acoustic channel within the bore, $v_s$ is the speed of sound through the medium and $v_m$ is the speed of the medium. Thus for an anticipated maximum speed of the medium of 10 m/s, the maximum anticipated change in the acoustic path length is approximately $I_b \cdot (1-330/340)$ or about 0.03 $I_b$. Thus $I_b$ should be less than 4 mm/0.03≈130 mm, so a path length of about 10 cm has been chosen in the present case.

Once the phase shift change is detected, this fact can be transmitted in the form of e.g. a radio signal back to the single operator at the head end of the conduit, such as a short message service (SMS) text message.

It is preferable to use as the acoustic signal an ultrasonic signal of about 40 kHz because this type of signal is inaudible to the human ear, and because small, inexpensive components for its transmission and reception are known and readily available, e.g. those manufactured by Farnell under parts number 213-214 (transmitter) and 213-226 (receiver). Thus it is within the scope of the invention to use any signal comprising a mechanical wave travelling through air as a medium, although of course practical considerations could intervene, e.g. the generation of an extremely low frequency wave may require a loudspeaker which is disproportionately large to the device itself.

The transducers could also be located within the device otherwise than described above within the housing, or be physically separate device(s) connected to the sensing device.

Figure 6A:
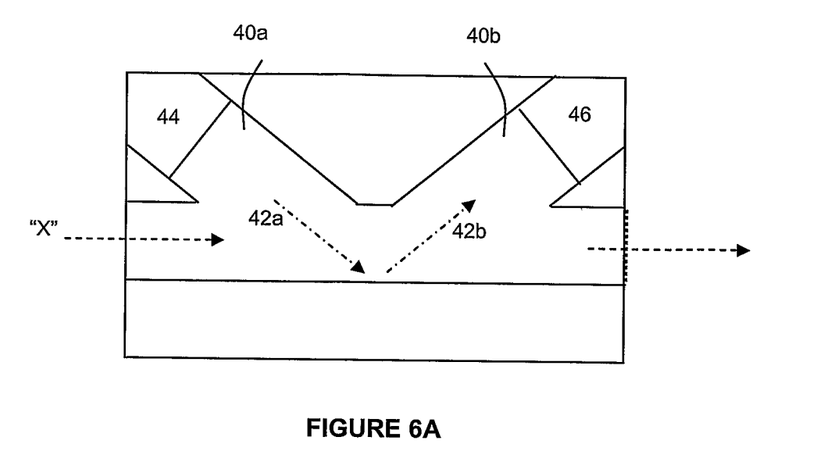
FIGS. 6A, 6B and 6C are alternative embodiments of the invention.

In one arrangement, the transducers could be sited at further within the acoustic channels as shown in FIG 6A. Alternatively, they could be sited at or very near to the interfacing section at which the device bore (34) and acoustic channels (42) intersect, and positioned thereat to direct the transmitted and received signals directly into the device bore. Thus, the acoustic channels are reduced in length or else rendered unnecessary: this would have the advantage of reducing the likelihood of air and/or the fibre unit from migrating into the acoustic channels, as well as obviating the need for acoustically-transparent barriers at the interface.

The frequency of 40 kHz for the acoustic signal is preferred because it has a wavelength of 7.5 mm which is ideal for the application and the anticipated air velocities in the bore. Furthermore, inexpensive off-the-shelf components for transmission and reception of such frequencies are known and readily available (e.g. those manufactured by Farnell mentioned above). This frequency is also inaudible to the human ear. However any signal comprising a mechanical wave of any frequency requiring air as a medium is within the scope of the invention. For example, if a wide range of air velocities was expected in the bore, a use of an acoustic signal with a lower frequency (and hence a larger wavelength) or of a shorter bore section of the acoustic channel, would be preferred (alternatively, the device could have a larger bore, thus causing a reduction in the speed of the air for a given total volume of air flowing through the bore per unit of time, etc.).

The barrier against which the reference sound wave signal is reflected also need not be located within the device bore, as long as the received signal is receivable by the receiver.

Yet other variations would also be clearly possible—the acoustic channel angles do not need to be set at 30 degrees to the axis of the device bore. This is a suitable angle permitting use of commonly-available and cheap transducers. It is also a sufficiently acute angle relative to the device bore (34) to permit the acoustic signal to travel along a sufficient distance along the bore to permit sensing of any air flow movement. Detection of air flow is still possible at less acute angles, but will tend to decrease as the angle between the axis of the bore and the channel(s) tend towards 90 degrees. To improve the sensitivity of the detection method, the bore could be made larger in diameter, or the acoustic signal used could be of a higher frequency.

This will permit the acoustic signal a longer period within the bore for the purpose of sensing air flow. Maximum sensitivity is at 0 degrees along the tube, although transducer placement within the tube may be a problem.

Figure 6B:
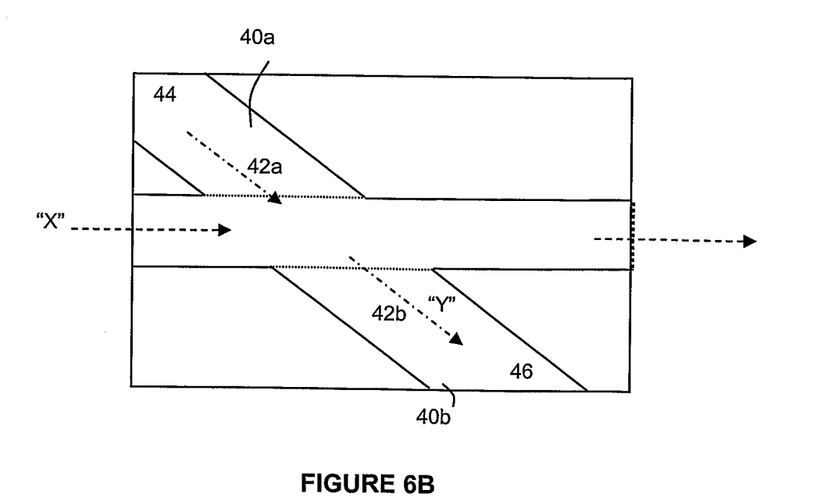
Figure 6C:
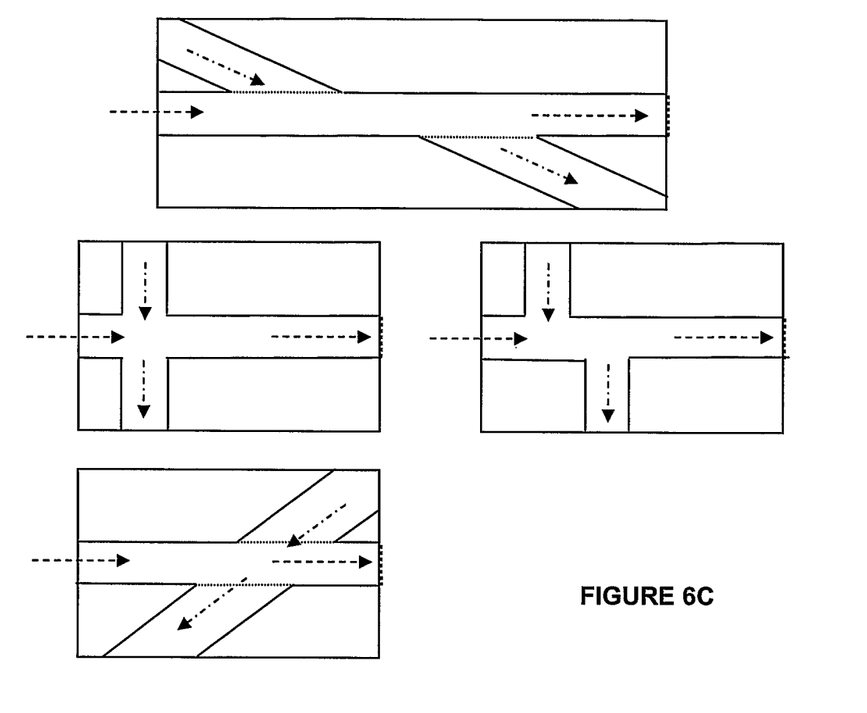

The skilled person would also recognise that the step of reflecting the acoustic signal (42) for measurement and comparison is not essential to detect any phase shifts indicating the presence of air flow in the device bore. For example, the acoustic channels could be arranged so that the transmitter is located in the transmission acoustic channel on one side of the bore, and the receiver in the reception channel on the other side of the bore as depicted in FIG 6B. In this embodiment, the signal (42a) transmitted by the transmitter (44) travels in the direction of arrow "Y" into the bore. Any air flow along the bore in the direction of arrow "X" will cause a phase shift in the acoustic signal received by the receiver (46) in the reception channel (40b). Various variations in the configuration of the acoustic channel are available: some are depicted in FIG 6C. Acute angles and right-angled acoustic paths can be off-set or not, and can also be arranged so that the acoustic signal is introduced into the bore against air flow direction, so that the signal is compressed instead. These may however increase the size of the housing required as compared to an embodiment of the invention using a reflected received signal.

It has been earlier noted that when air has been confirmed to be flowing to and from the remote end of the conduit by the device, a preferably radio signal is sent to the operator at the head end. Upon receipt of this signal, the fibre unit can be fed into the tube confirmed to have been correctly identified at the head end. The device of FIG 4 and the methods used can also be used to detect the arrival of the fibre unit at the remote end.

It is expected that when air flow reaches the device bore (34), the acoustic signal will change a first time to mark this. The signal should remain relatively steady in its phase shifted state for as long as the air continues to flow within the bore at a relatively steady velocity. When the fibre unit arrives in the bore of the device, the acoustic signal is changed a second time. For example, the fibre, or the bead (e.g. B in FIG 2) attached to fibre end, may restrict or block the air flow within the bore. The receiver can detect this further phase shift, which may be interpreted as an indication that the fibre unit has arrived within the sensing device at the remote end of the conduit.

Cost-savings can be realised by using the same sensing device and the method to detect the arrival of air, and subsequently the arrival of the fibre unit.

Although the device and method are described to be deployed at the remote end as shown in FIG 3B, to enable determination that air and fibre reaches the remote end, they can be also used for other purposes. For example, the device could be fashioned as a sleeve to be used as a connector at intermediate points along the conduit route, for detection of the path taken by the air flow. This allows the operator to track the progress and movement of the air and the fibre unit for purposes in addition to, or other than for, installing blown fibre—such as in the detection of gaps leading to air leaks in the conduit tube network.

By providing some mechanism for enabling an acoustic signal to enter and exit a conduit, a device could be created which can be placed at any point along a conduit to determine if air is flowing through it, without having to pierce the conduit. For example, it could be possible to simply use a quite strongly amplified transmitter and a dampening mechanism for preventing the acoustic signal passing through the conduit wall or the exterior of the conduit, alternatively some sort of gel or other material could be used to form acoustic windows into the conduit.

The device could also be used to measure the velocity of air travelling within tubes and conduits if suitably calibrated. The phase shift of the acoustic varies with speed, so that as speed increases so does the phase shift because the acoustic path gets stretched with increasing speed or compressed with decreasing speed.

Although developed specifically for detection of air flow arrival and speeds in the particular context of the installation of blown fibre, the skilled person would realise the applicability of the apparatus and methods in other contexts and industries concerned with the detection of fluid flow and speed, such as within conduits and pipes for gas, water or oil.

Figure 7:
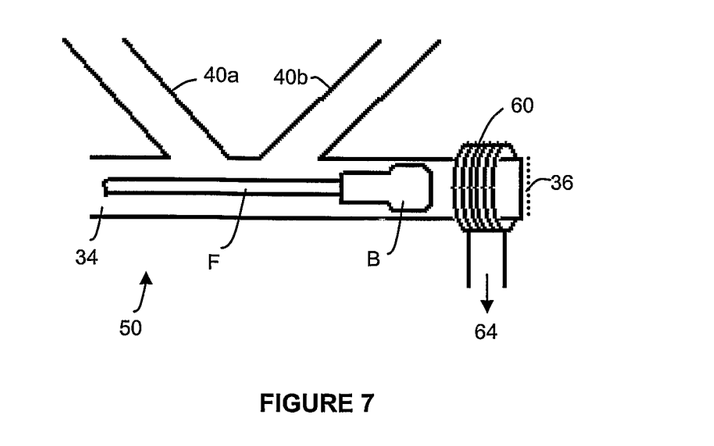
FIG 7 depicts an embodiment of a device for sensing air and fibre unit arrival.

Turning back to the context of a blown fibre installation, the above device and method can advantageously be used with components and methods that will positively indicate arrival of the fibre unit at the device. FIG 7 shows an embodiment of the device of FIG 4, further including the components for the aspect of the device which allow detection of arrival of the fibre unit within the device, which is based on detection of the presence of the metal bead (e.g. B in FIG 2) coupled to the end or tip of the fibre unit.

In FIG 7, the device bore (34) as described previously, terminates in an air-porous barrier (36). An induction loop (60) acting as a metal detector or sensor to detect the presence (or absence) of the bead, is positioned at or near the air-porous barrier. As is well known, induction loop detection is based on changing inductance which changes the frequency of an oscillator of which the inductive loop forms a part. The sensor in its most basic form consists of an oscillator producing an alternating current that passes through a coil producing an alternating magnetic field. A bead made of metal, which is electrically conductive, close to the coil will induce eddy currents in the metal, and this produces an alternating magnetic field of its own.

Here, the sensor takes the form of a coil of copper which is wrapped around the bore at or near the far terminal end as shown in FIG 7. The loop forms part of an LC oscillator (64), which resonates at a constant frequency $\omega_0 = 1/(LC)^{1/2}$. In the present embodiment, a Hartley oscillator is used in which both the frequency, and amplitude of oscillation are affected if there is a change in the inductance and quality (Q value) of the oscillator. Preferably the wall of the bore should be as thin (e.g. about 1 mm thick) and/or the coil wrapped as closely to the bore to attain the greatest sensitivity of the coil to the presence of the metal bead which serves as an actuator for the induction detection system and the coil in particular.

The induction loop is made of a coil of preferably very fine copper wire having a diameter of about 0.2 mm, wound about 10 to 20 times around the bore. However the exact number of turns is not critical to invention, nor is the size of the wire, although the number of turns used is related to the coil diameter.

Prior to installation, a bead (B) is attached to the fibre unit (F). In this aspect of the invention, the bead must include some metal or some other material with a relatively high permeability and/or conductivity. When the fibre unit arrives at the remote end of the conduit, it travels out of the tube (T2 in FIG 3B) and into the sensing device (50) along the bore (34). Its progress is finally halted when the beaded end of the fibre unit reaches the porous barrier (36) which permits air to escape, but retains the fibre unit within the bore. At this point, the metal bead (B) is lodged within close proximity of the induction coil (60) and serves as an electromagnetic actuator to the sensing device, by acting as a metallic core which changes the inductance of the coil and the Q-value of the oscillator. The changes in inductance and Q-value cause both frequency and amplitude to vary, so either or both of which can therefore be monitored and measured. As the change in amplitude is greater with the preferred type of bead used in the present embodiment, however, it is easier and preferable to monitor this. The change is detected by a comparator and is a clear indication of the arrival of the beaded fibre unit. An alert can then be signalled back to the single operator at the head end of the conduit, allowing him to terminate the installation session. This can be performed in a variety of ways, including the use of radio frequency signals. In a preferred embodiment, a short message service (SMS) text message can be sent back to the head end where the installing personnel is located, providing clear confirmation that the fibre has been installed through the length of the tube or conduit and had reached the far end—instead of being e.g. stuck in a location half way to the far end.

Variations within the scope of the invention are possible. For example, the coil is located at or near the end of the bore so as to realise the advantage of a continuous reading of the bead's presence as the metal core within the coil. This allows for an unambiguous indication of the bead's arrival within the bore. However, location of the coil elsewhere in the device—indeed, location anywhere else within the conduit—would allow for the detection of the momentary change in the inductance in the coil indicating that the bead has passed through it. As with the ultrasonic phase shift detection method described above, this could allow an operator to track the progress and movement of the beaded fibre unit along the conduit and/or conduit network. For example, the bore of the device may be configured to extend and taper beyond the housing (32) so that upon arrival, the beaded fibre unit comes to a rest within a narrower section of the bore so that the coil (60) can be actuated by the presence of the bead acting as a metallic core.

Different materials will cause the oscillator to resonate at different frequencies. In the present embodiment, the coil responds to the arrival of beads made from various metals such as aluminium, brass, steel or copper. The applicants currently use a bead made of aluminium in preference to iron-based metals as auminium is cheap, lightweight and does not rust. Aluminium is a third less dense than steel, and less expensive and easier to manufacture than brass.

Where corrosion is less of an issue, alternative fibre unit arrival detection methods within the scope of the invention can be realised. For example, by substituting the induction coil with a magnetic sensor, the arrival of a bead made of a magnetic material (which need not include metal) or otherwise a ferrous material (any material exhibiting strong ferro- or para-magnetism characteristics should be suitable) could be detected as a Hall probe causing a change in the magnetic flux of the magnetic sensor. This change can again be sent to the operator using e.g. a radio link. The skilled person may realise yet other implementations of the detection method, such as using electromagnetic proximity sensing methods, for example by sensing the change in the capacitance of a capacitor formed so as permit the bead to pass between the plates of the capacitor, in which case the bead should be made of a material having a relatively high dielectric constant.

In the current application in the context of blown fibre installations, use of a sensing method with no moving parts is particularly advantageous. This is because air flows and movements within the tube could be disturbed by a moving sensor device. The sensor itself could be affected by the air, as well as by debris and particularly the microspheres which coat the fibre units (which enhance the effect of viscous drag during installation, and which could fall off and blown along the conduit by the pressurised air). In an even more preferred embodiment the sensor is contactless as so that it can be placed outside the conduit tube (where the device is to be placed at the intermediate section of the conduit without need to pierce the tube) or the bore of the device, as shown in FIG 7. However in other applications it would certainly be possible to place the sensing device within the conduit or bore, or other containment device or otherwise, to realise the purpose of the invention. By doing so, it is also possible in some embodiments of the invention to track the speed at which the actuator bead is travelling within the conduit.

Yet other variations would be apparent to the skilled person: for example, the sensing device need not be located right next to the conduit or bore; it could be located some distance away if it is sufficiently sensitive to the movement of the actuating bead. Also, the locations of the sensing device and the actuator could be reversed, so that the sensor is placed on the fibre unit at its tip or elsewhere along its length, and the actuator placed within, around or proximate to the conduit or tube through which the fibre unit will travel. The principle of the invention requires only that the sensor detects the actuator and registers the change in the electromagnetic property.

The invention does not require that the actuator be coupled to a fibre unit or indeed any object at all. A system can be set up so that the proximity of the electromagnetic actuator to the sensor can have the significance of indicate presence or movement. Accordingly, it is possible to use this aspect of the invention to detect e.g. movement and/or presence of air or such other medium carrying the actuator, which could be made very lightweight and/or mobile by the provision of e.g. wheels of skids.

As noted above, alerts are sent from the remote end to the operator at the head end to alert or inform him about the arrival of air or of the fibre unit at the sensing device. This is conveniently implemented using radio signals, which can be transmitted to e.g. a hand held device. Alternatively the receiving device could be integral to a piece of equipment used at the head end, e.g. the blowing head and/or the compressor. It is possible also to automate this part of the process, so that upon receipt of a signal that air has arrived at the remote end, the blowing head could start plying fibre into the conduit; or the apparatus shutting themselves off upon receipt of a signal that the fibre unit has arrived.

As noted above, the size of the housing of the device is about the size of a matchbox (dimensions very approximately 55 mm×35 mm×15 mm), within which is fitted the transmitter and receiver, and the induction coil.

A power source (e.g. a battery) is also included, as is a radio unit and antenna for sending confirmatory signals to the head end of the conduit. A printed circuit board is installed along a wall of the housing, which may include a processor, for detecting, comparing etc. the acoustic signals for a phase shift, and for determining any inductance change in the coil. The skilled person would appreciate that some or all of these components could comprise separate apparatus or devices sited outside the housing but connected thereto. The embodiment of the invention as shown in FIG 7 is designed for use at the remote end of the conduit to detect fibre arrival. However, as discussed in connection with the phase shift detection aspect of the device, this proximity sensor—preferably a contactless version—could also be placed non-invasively at any point around a conduit to detect the passing of a suitable bead through the conduit at that point.

Figure 8:
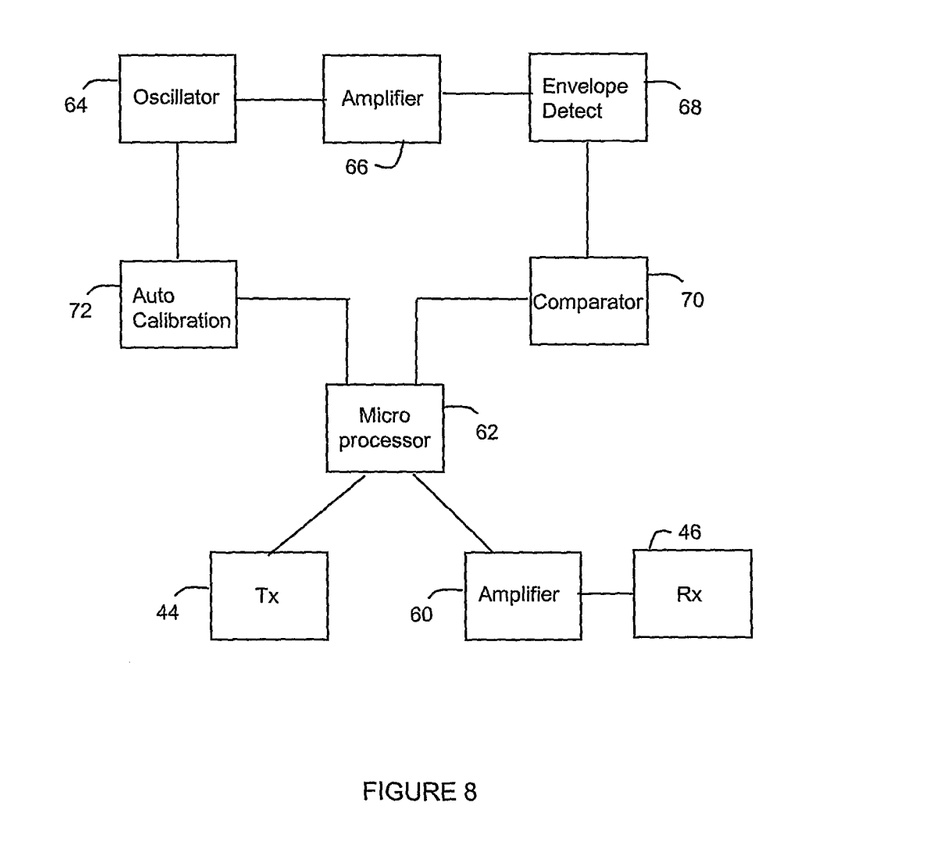
FIG 8 is a schematic view of components making up an embodiment for sensing air and fibre unit arrival.

FIG 8 is a bock diagram showing the basic elements making up an embodiment of the sensing device (30) discussed above, comprising an air arrival detection component, and a fibre bead arrival component. This will be described in conjunction with FIG 7.

The air sensing component comprises the transmitter (44) and receiver (46) which are respectively located in the transmission channel (40a) and receiving channel (40b) shown in FIG 7. The air detection part of the sensing element (30) is coupled to a processor (62) which performs the computations necessary to detect a phase shift indicating arrival of air into the sensing device. The signal from the receiver (46) is passes through amplifier (60) to ease the processor's task.

The fibre bead detection component of the sensing element (30) is made up of an oscillator (64) of which the induction loop (64, in FIG 7) is a part. The oscillator resonates at a constant frequency e.g. at 1 Mhz. The signal is amplified with an amplifier (66) and any changes in the signal are picked up by an envelope detector (68) and comparative device (70). The changes are analysed by the processor (60) and any change in the signal from the oscillator (which can include the current, frequency, or amplitude) can signal detection of a metallic object such as an aluminium bead.

The methods, devices and configurations described above and in the drawings are for ease of description only and not meant to restrict the invention to any particular embodiments. It will be apparent to the skilled person that various sequences and permutations on the methods and devices described are possible within the scope of this invention as disclosed; similarly the invention could be used in various similar scenarios and for various cable types. In particular, the apparatus and methods relating to air flow detection by ultrasound phase shift detection and the methods and apparatus relating to fibre unit arrival detection by detection of phase shift and/or a electromagnetic property in e.g. a coil, are depicted in this description to be used together advantageously in a preferred embodiment. However they will work independently of each other on their own, to realise the advantages of the respective inventions.

The invention claimed is:

1. A device for detecting presence of a cable provided with a metallic attribute at a remote end of a conduit, the device comprising:
   a housing, comprising an air-porous barrier, the housing being configured in use to enable a cable entering the housing to be contained within the housing; and
   a sensing unit configured to sense the metallic attribute of the cable contained within the housing, by sensing a change in inductance levels of the sensing unit.

2. The device according to claim 1 wherein the housing is configured to contain the cable in a position outside the conduit.

3. The device according to claim 1 wherein the metallic attribute comprises a bead secured to the leading end of the cable.

4. The device according to claim 1 wherein the sensing unit comprises an LC oscillator including an induction loop.

5. The device according to claim 4 wherein the sensing unit is located so that in use the metallic attribute of the cable is contained within the housing in close proximity of the induction coil.

6. The device according to claim 1 further including unit configured to send a confirmatory signal upon sensing of the metallic attribute.

7. The device according to claim 1 further comprising a detector to detect air flow within the housing.

8. A system for installing a cable provided with a metallic attribute using an air flow into a conduit, the system comprising:
   an air source configured to introduce air flow through the conduit towards a remote end of the conduit;
   a driving unit configured to mechanically drive the cable through the conduit towards the remote end of the conduit; and
   a device configured to detect presence of the cable provided with the metallic attribute at the remote end of the conduit, the device comprising:
      a housing, comprising an air-porous barrier, the housing being configured in use to enable the cable entering the housing to be contained within the housing; and
      a sensing unit configured to sense the metallic attribute of the cable contained within the housing, by sensing a change in inductance levels of the sensing unit.

9. A method for detecting presence of a cable provided with a metallic attribute at a remote end of a conduit, the method comprising
   providing a device configured to detect presence of the cable provided with the metallic attribute at a remote end of the conduit, the device comprising:
      a housing, comprising an air-porous barrier, the housing being configured in use to enable the cable entering the housing to be contained within the housing; and
      a sensing unit configured to sense the metallic attribute of the cable contained within the housing, by sensing a change in inductance levels of the sensing unit;
   attaching the housing of the device to the remote end of the conduit;
   installing the cable through the conduit; and
   sensing the metallic attribute of the cable contained within the housing, by sensing a change in inductance levels of the sensing unit.

10. The method according to claim 9 further comprising sending a confirmatory signal upon sensing of the metallic attribute.

11. The method according to claim 9 further comprising detection of air flow within the housing.

* * * * *